United States Patent [19]

Shibagaki et al.

[11] Patent Number: 5,041,566

[45] Date of Patent: Aug. 20, 1991

[54] METHOD OF PREPARING LEVOGLUCOSENONE

[75] Inventors: Makoto Shibagaki; Kyoko Takahashi; Hideyuki Kuno; Ichiro Honda; Masataka Mori; Hajime Matsushita, all of Yokohama, Japan

[73] Assignee: Japan Tobacco Inc., Tokyo, Japan

[21] Appl. No.: 578,142

[22] Filed: Sep. 6, 1990

[30] Foreign Application Priority Data

Sep. 6, 1989 [JP] Japan .................................. 1-229344

[51] Int. Cl.$^5$ ............................................ C07D 311/94
[52] U.S. Cl. ...................................... 549/397; 549/386
[58] Field of Search ................................ 549/397, 386

[56] References Cited

U.S. PATENT DOCUMENTS 3,926,947 12/1975 Lipoka ................................. 549/397

*Primary Examiner*—Nicky Chan
*Attorney, Agent, or Firm*—Birch, Stewart, Kolasch & Birch

[57] ABSTRACT

Levoglucosenone is prepared by reaction sequence using 1,6-anhydro-β-D-galactopyranose as a starting material. First, the starting material is reacted with ortho formate, obtaining an ortho ester of said starting material. Then, the ortho ester is placed under the conditions for a reductive elimination reaction of the ortho formate part of said ortho ester, thereby converting said ortho ester to a 1,6-anhydro-3,4-dideoxy derivative. The dideoxy derivative is placed under the conditions for oxidation of the hydroxy group of said dideoxy derivative, thereby forming levoglucosenone.

13 Claims, No Drawings

METHOD OF PREPARING LEVOGLUCOSENONE

BACKGROUND OF THE INVENTION

1. Field of the Invention

The present invention relates to a novel method of preparing levoglucosenone (1,6-anhydro-3,4-dideoxy-β-D-glycero-hex-3-enopyranos-2-ulose).

2. Description of the Prior Art

Levoglucosenone is known as a sugar derivative. This is an optically active organic compound in which all carbon atoms are different environments and which has easily modifiable functional groups. Having these characteristics, levoglucosenone is a very useful compound for organic synthesis. As has been proved, it can be utilized as the starting material in the synthesis of 2,3-dideoxyribose which is useful as a medicine or the like. Also, levoglucosenone is used as the starting material for synthesizing optically active compounds, as is disclosed in Carbohydr. Res., 61, 519 (1978); 71, 169 (1979); 114, 71 (1983).

As has hitherto been known, levoglucosenone can be prepared by thermally decomposing cellulose. (See Carbohydr. Res., 61, 519 (1978); 67, 433 (1978), J.C.S. Perkin Trans. 1, 49 (1988), and U.S. Pat. No. 3,926,947 etc.). Also, it can be prepared by thermally decomposing cotton, chitin, glucose, or the like, as is disclosed in J. Macromol, Sci. Chem., A21, 385 (1984), Angew.-Chem., 90, 802 (1978), and Carbohydr. Res., 46, 149 (1976).

These conventional methods have following disadvantages. First, they can provide but a low yield of 5% or less. Second, they makes a great amount of a reaction residue as by-product. Third, they require high thermal decomposition temperatures of 300° C. or more. Fourth, it is difficult to heat the material uniformly since the material is a solid such as cellulose. In view of these disadvantages, the conventional methods are regarded as not suitable for preparation of levoglucosenone on an industrial scale.

On the other hand, as is known in the art, 1,6-anhydro-β-D-galactopyranose identified by formula (4) can be prepared easily with a high yield from D-galactose which is abundant in nature and identified by formula (1), by the method represented by the following scheme I, as is disclosed in Berichte, 687 (1929), J. Am. Chem. Soc., 64, 2435 (1942); *Chemistry of the Carbohydrates.* Acad. Press, N.Y., p. 214 (1948); and Chem. Ind., 1637 (1967) etc.:

Scheme I

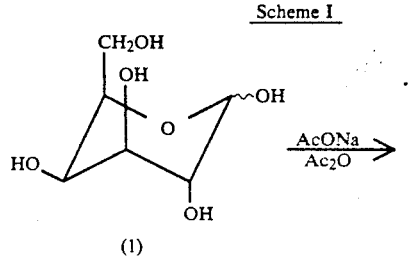

(1)

-continued
Scheme I

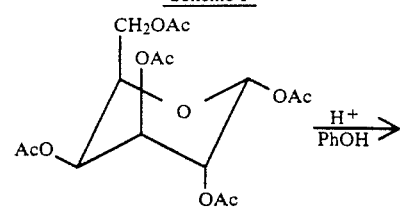

(2)

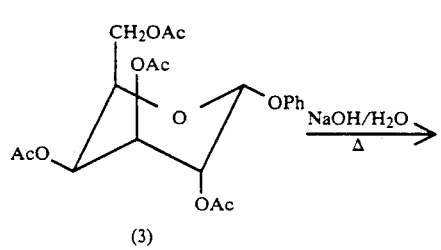

(3)

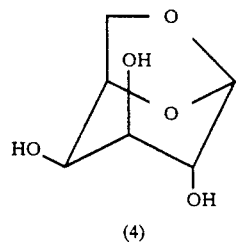

(4)

Also, it is known that 1,6-anhydro-3,4-dideoxy derivative identified by formula (6') can be obtained starting from 1,6-anhydro-β-D-galactopyranose (4). In this method, as is represented by scheme II, 2-mesylorthoester identified by formula (5') which has been prepared from the starting material (4) is thermally decomposed at 170° C. (see Natural and Applied Science Bulletin, Vol. 32, 1-4 (1980)). This method, however, requires five reactions steps, 1,6-anhydro-3,4-dideoxy derivative (6') which is the final product, is obtained from the starting material (4). Moreover, since the 2-mesylorthoester (5') is thermally decomposed at high temperature of 170° C., the 1,6-anhydro-3,4-dideoxy derivative (6') is prepared, but at an extremely low yield of about 4%.

Scheme II

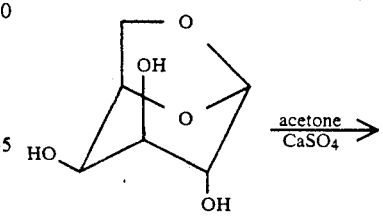

(4)

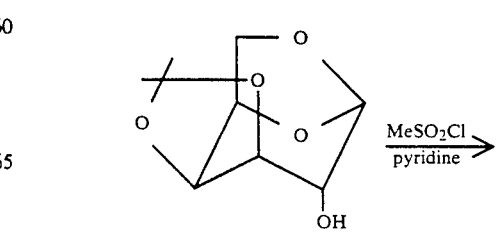

-continued
Scheme II

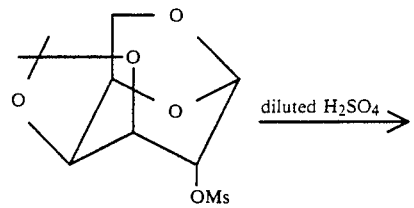

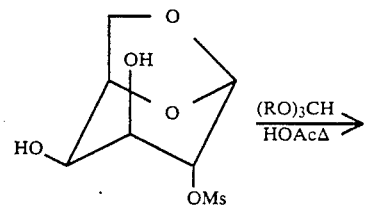

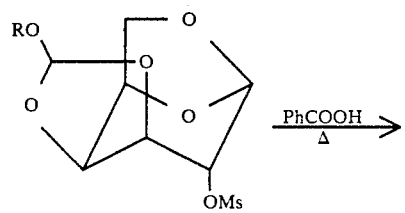

R = CH₃ or C₂H₅
(5')

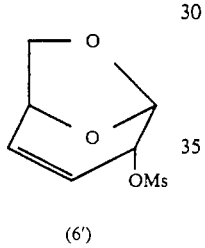

(6')

As is pointed out in Natural and Applied Science Bulletin, it is difficult to obtain the ortho ester (5') directly from the starting material (4), and then to convert this ortho ester (5') to 1,6-anydro-3,4-dideoxy derivative (6').

SUMMARY OF THE INVENTION

The object of the present invention is to provide a method of preparing levoglucosenone easily at high yield on an industrial scale, starting from a material which is readily available.

The object can be attained through a single reaction, by reacting an ortho formate with 1,6-anhydro-β-D-galactopyranose, thereby producing an ortho ester of 1,6-anhydro-β-D-galactopyranose with ease and at a high yield.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

DETAILED DESCRIPTION OF THE PREFERRED EMBODIMENTS

We had been repeating experiments in an effort to prepare levoglucosenone starting from 1,6-anhydro-β-D-galactopyranose easily at a high yield. As a result we found it possible to prepare the ortho ester (5) of the starting material (4), easily at a high yield, through a single reaction step, by reacting an ortho formate with the starting material (4) as is illustrated by the following scheme III. More specifically, ortho formate is reacted with 1,6-anhydro-β-D-galactopyranose (4), thereby preparing the ortho ester (5). Then the ortho formate part of the ortho ester (5), thus obtained, is subjected to reductive elimination reaction, thereby forming a 2-hydroxy dideoxy derivative (7) of the starting material. Then, the hydroxy group of the 2-hydroxy dideoxy derivative (7) is oxidized, thereby preparing levoglucosenone (8).

Scheme III

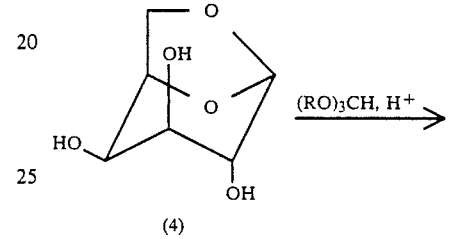

(4)

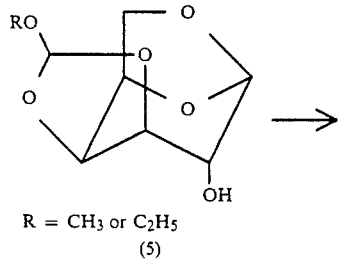

R = CH₃ or C₂H₅
(5)

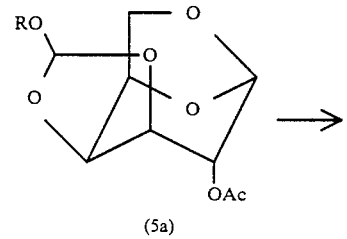

(5a)

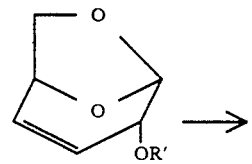

R' = CH₃CO or CHO
(6)

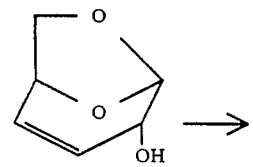

(7)

-continued
Scheme III

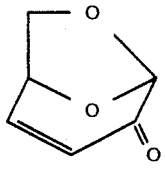
(8)

The reaction between an ortho formate and 1,6-anhydro-β-D-galactopyranose (4) can be appropriately carried out in an aprotic polar solvent, which may be N,N-dimethylformamide, tetrahydrofuran, 1,4-dioxane, diglyme, or the like. Although the ortho formate used is not particularly limited, ethyl or methyl ortho formate, either readily available, is usually preferred.

It is desirable that the reductive elimination of the ortho formate part from the ortho ester (5) is performed by heating the ortho ester (5) in the presence of an inorganic solid catalyst or an organic acid. The inorganic solid catalyst can be hydrous zirconium oxide as is disclosed in Published Unexamined Japanese Patent Application No. 61-204143. Alternatively, it can be silica gel, alumina or the like. The organic acid can be acetic acid, formic acid or the like.

The hydroxy group of the 2-hydroxy dideoxy derivative (7), thus obtained as mentioned above, is oxidized, thus preparing levoglucosenone (8). The oxidation of the hydroxy group of the 2-hydroxy dideoxy derivative (7) can be accomplished by using an oxidizing reagent, which can be, for example, active manganese dioxide.

The method according to the present invention will now be described in greater detail.

First, 1,6-anhydro-β-D-galactopyranose (4) is prepared from D-galactose by the known method which will be later described as referential example. It is true that 1,6-anhydro-β-D-galactopyranose (4), thus obtained, can be subjected directly to the next reaction step, but this compound should better be refined by converting into a triacetate of this compound. Then, one part by weight of 1,6-anhydro-β-D-galactopyranose (4) is added to 2 to 20 parts by weight, preferably 5 parts by weight, of an aprotic polar solvent, together with 2 to 10 parts by weight, preferably 5 parts by weight, of an ortho formate, thereby preparing a solution. This solution is stirred, along with a small amount of acid such as sulfuric acid or acetic acid for 1 to 12 hours at room temperature, whereby 1,6-anhydro-β-D-galactopyranose (4) reacts with an ortho formate. As a result of this, a reaction product is formed. Next, a small amount of aqueous sodium hydrogencarbonate solution is added to the solution, thereby neutralizing the reaction mixture. The reaction product is then extracted with an organic solvent such as dichloromethane or chloroform. The resultant extract is dried with sodium sulfate or the like. Further, the solvent is distilled off, under reduced pressure, thereby obtaining the ortho ester (5). The ortho ester (5) may be subjected to O-acetylation in the known manner, thus converting into colorless crystal of the acetate identified by formula (5a). The O-acetylation is an effective means for purification.

Next, one part by weight of the ortho ester (5), thus obtained, is dissolved in 3 to 20 parts, preferably 10 parts, by weight of a solvent, thereby preparing a reaction solution. The solvent may be a polar solvent. Then, 0.01 to 0.5 parts by weight, preferably 0.1 part by weight, of an inorganic solid catalyst or an organic acid is added to one part by weight of the reaction solution. The reaction solution is left to stand at 40° C. to the boiling point of the used solvent, preferably 130° C., for 2 to 12 hours, thus causing desired reaction. The reaction mixture is neutralized with aqueous sodium hydrogencarbonate solution and then extracted with an organic solvent such as ether, dichloromethane, or chloroform. The resultant extract is dried with sodium sulfate or the like. Then, the solvent is distilled off under reduced pressure. The residue thus obtained is further distilled at certain temperature, for example, at 64° C. under reduced pressure of 2 mmHg, thereby obtaining the 2-hydroxy dideoxy derivative (7).

In the above step, when the purified acetate (5a) in place of the ortho ester (5), 1,6-anhydro-3,4-dideoxy-2-acethyl-β-D-galactopyranose (6) is obtained by the reaction described above. In addition, in the case of using acetic anhydride or N,N-dimethylformamide as a solvent in the reductive elimination described above, the dideoxy derivative (6) which is acetate or formate is obtained as an intermediate. The intermediate may be isolated. Whichever, the dideoxy derivative (6) is converted into the 2-hydroxy dideoxy derivative (7) by the following procedure.

One part by volume of the dideoxy derivative (6), S thus obtained, is dissolved in 5 to 20 parts by weight, preferably 10 parts by weight, of methanol or ethanol, preparing a solution. A small amount of sodium methoxide, sodium hydroxide, potassium carbonate, or the like is added to this solution. The solution is subjected to reaction at room temperature for 1 to 4 hours. Then, the solvent is distilled off under reduced pressure, and the residue is extracted with an organic solvent such as ether, dichloromethane or chloroform. The extract is dried with sodium sulfate or the like. Next, the solvent is distilled off under reduced pressure, thereby quantitatively obtaining the 2-hydroxy dideoxy derivative (7), i.e., 1,6-anhydro-3,4-dideoxy-β-D-galactopyranose (7).

Thereafter, one part by weight of the 2-hydroxy dideoxy derivative (7) is dissolved in 10 to 50 parts by weight, preferably 20 parts by weight, of an organic solvent, preferably dichloromethane, thus forming a solution. 3 to 20 parts by weight of an oxidizing reagent, preferably 5 parts by weight thereof, is added to the solution thus prepared, thereby forming a mixture. This mixture is stirred at room temperature for 1 to 5 hours, thus causing a reaction in the mixture. Then, the oxidizing reagent is filtered off, and the solvent is distilled off under reduced pressure, whereby levoglucosenone (8) is obtained.

The method according to this invention will now be explained in still greater detail, with reference to several examples and a referential example.

REFERENTIAL EXAMPLE

Synthesizing of 1,6-anhydro-β-D-galactopyranose

First, 800 ml of acetic anhydride was refluxed, along with 15 g of sodium acetate, thus preparing refluxed liquid. Then, 15 minutes later, 10 g of D-galactose anhydride (1) was added to the refluxed liquid, five times, while agitating the refluxed liquid, thus adding 50 g of D-galactose anhydride (1) in total. After completion of the reaction, the reaction mixture was poured into 5 % of iced water and agitated, whereby a white solid was precipitated. The solid was recrystallized from hot methanol, thereby resulting 98 g of needle-shaped crystal of 1,2,3,4,6-pentaacetyl-β-D-galactopyranose (2) was obtained. This substance exhibited the following physical properties:

Pentaacetyl-β-D-galactopyranose (2)

$^1$H NMR (ppm from TMS): CH$_3$CO; 2.00 (3H,s), 2.05 (6H,s), 2.13 (3H,s), 2.17 (3H̄,s), 1-position; 5.70 (1H,d,J=8.22Hz), 2-position; 5.34 (1H,dd,J=8.22, 10.55Hz), 3-position; 5.08 (1H,dd,J=3.16, 10.55Hz), 4-position; 5.43 (1H,d,J=3.16Hz), 5-position; 4.07 (1H,dd,J=5.03, 10.44Hz), 6-position; 4.14 (1H,m), 4.16 (1H,m)

$^{13}$C NMR (ppm from TMS): 1-position; 92.4, 2- or 3-position; 71.0, 72.0, 4- or 5-position; 67.0, 68.1, 6-position, 61.3, CH$_3$CO; 21.0, 21.8, CH$_3$C̄O; 169.0, 169.4, 170.0, 170.1, 170.3 m.p.; 140.5° to 141.5° C..

$[\alpha]_\alpha^{25} = +26.7$ (c=0.975, chloroform)

98 g of the pentaacetate (2), thus obtained, was dissolved in 96 ml of hot phenol, forming a solution. Then, 1.3 g of para-toluene sulfonic acid (monohydrate) was added to the solution, thus causing a reaction in the solution at 100° C. for 30 minutes under reduced pressure of 40 mmHg. After almost all acetic acid had been distilled off, the pressure was reduced to 10 mmHg, and the reaction was continued for other 30 minutes. Then, 28 ml of hot phenol containing 0.45 g of sodium hydroxide was added to the reacted solution, preparing a mixture liquid. This mixture liquid was heated for 30 minutes under a pressure of 2 mmHg. After most phenol had been distilled off, the mixture liquid was poured into 2 % of hot water, and the resultant mixture was agitated to precipitate a yellowish brown solid. Then, the solid was recrystallized from hot ethanol, thereby obtaining 110 g of needle-shaped white crystal of phenyl-2,3,4,6-tetraacetyl-β-D-galactopyranoside (3) at a yield of 94%. This product exhibited the following physical properties:

Phenyl-2,3,4,6-tetraacetyl-β-D-galactopyranoside (3)

$^1$H NMR (ppm from TMS): CH$_3$CO; 2.02 (3H,s), 2.06 (3H,s), 2.07 (3H,s), 2.19 (3H̄,s), 1-position; 5.06 (1H,d,J=7.96Hz), 2-position; 5.50 (1H,dd,J=7.96, 10.46Hz), 3-position; 5.12 (1H,dd,J=3.43, 10.46Hz), 4-position; 5.46 (1H,dd,J=3.43, 0.86Hz), 5-position; 4.08 (1H,ddd,J=0.86, 6.10, 7.10Hz), 6-position; 4.20 (1H,dd,J=6.10, 11.17Hz), 4.24 (1H,dd,J=7.10, 11.17Hz).

$^{13}$C NMR (ppm from TMS): 1-position; 99.9, 2- or 3-position; 71.0, 71.2, the 4- or 5-position; 67.1, 68.9, 6-position, 61.5, CH$_3$CO; 20.8, phenyl group; 157.1, 117.1, 123.4, 129.6, CH$_3$C̄O; 169.3, 170.0, 170.3, 170.3 m.p.; 122.0° to 122.5° C.

$[\alpha]_\alpha^{25} = +6.3$ (c=1.085, chloroform)

110 g of the tetraacetate (3), thus obtained, was added to 500 ml of 3N aqueous solution of sodium hydroxide, and the resultant mixture solution was heated and refluxed for 5 hours. The refluxed and reacted solution was cooled and neutralized with 50%.%-sulfonic acid. Thereafter, the solvent was distilled off under reduced pressure. The residue was extracted from the solution, by using hot ethanol. Further, the solvent was distilled off from the extract under reduced pressure, thereby obtaining 1,6-anhydro-β-D-galactopyranose (4) in the form of a crude mixture.

1,6-anhydro-β-D-galactopyranose (4), thus obtained, which was in the form of a crude mixture, was added to 100 ml of acetic anhydride, thus preparing a solution. This solution was heated and refluxed for 1 hour, thus causing a reaction. Then, water was added to the reacted solution, an excess of acetic anhydride was hydrolyzed, and the solvent was distilled off under reduced pressure. Next, chloroform was added to the residue, thereby obtaining an extract. This extract was washed with water and dried with sodium sulfate. The solvent was distilled off under reduced pressure, obtaining light yellow oily substance. This oily substance was left to stand in ether at 0° C. for 12 hours, whereby 58 g of needle-shaped white crystal of 1,6-anhydro-2,3,4-triacetyl-β-D-galactopyranose (4) at a yield of 76%. This substance exhibited the following physical properties:

1,6-anhydro-2,3,4-triacetyl-β-D-galactopyranose (4)

$^1$H NMR (ppm from TMS): CH$_3$CO; 2.03 (3H,s), 2.13 (3H,s), 2.13 (3H,s), 1-position; 5.43 (1H,s), 2-position; 4.75 (1H,t,J=1.33Hz), 3-position; 5.24 (1H,m), 4-position; 5.25 (1H,m), 5-position; 4.47 (1H,ddd,J=1.10, 4.82, 5.01Hz), 6-position; 4.34 (1H,d,J=7.38Hz), 3.74 (1H,dd,J=5.01, 7.38Hz).

$^{13}$C NMR (ppm from TMS): 1-position; 99.0, 2-position; 71.2, 3-position; 67.6, 4-position; 64.9, 5-position; 72.2, 6-position; 64.5, CH$_3$CO; 20.8, 20.7, 20.6, CH$_3$C̄O; 169.2, 169.4, 169.4 m.p.; 72.5° to 73.5° C.

$[\alpha]_\alpha^{25} = -4.7$ (c=0.90, chloroform)

Thereafter, the triacetate, thus obtained, was added to 100 ml of methanol, and a small amount of sodium methoxide was also added to methanol, thus preparing a solution. This solution was agitated for 1 hour, thus causing a reaction. Cation exchange resin was added to the reacted solution, and the solution was stirred for 10 minutes. The insoluble substance was filtered off, and the solvent was distilled off under reduced pressure. The residue was recrystallized from 2-propanol, thereby obtaining 32 g of solid white substance of 1,6-anhydro-β-D-galactopyranose (4) at a yield of 100%. The substance, thus obtained, had the following physical properties:

6-anhydro-β-D-galactopyranose (4)

$^1$H NMR (ppm from TMS): 1-position; 5.24 (1H,t,J=1.5Hz), 2-position; 3.65 (1H,t,J=1.6Hz), 3-position; 3.83 (1H,dq,J=5.0, 1.5Hz), 4-position; 3.94 (1H,dd,J=5.0, 4.3Hz), 5-position; 4.30 (1H,dd,J=4.3, 5.0Hz), 6-position; 4.32 (1H,d,J=7.0Hz), 3.53 (1H,ddd,J=1.5, 5.0, 7.0Hz).

$^{13}$C NMR (ppm from TMS): 1-position; 102.7, 2-position; 73.2, 3-position; 72.3, 4-position; 65.8, 5-position; 76.0, 6-position; 64.4 m.p.; 200.5° to 201.5° C.

$[\alpha]_\alpha^{25} = -28.3$ (c=0.40, water)

EXAMPLE 1

[A]32 of 1,6-anhydro-β-D-galactopyranose (4) was added, along with 66 g of ethyl ortho formate, to 120 ml of N,N-dimethylformamide, thus preparing a mixture liquid. A drop of concentrated sulfuric acid was added to this mixture liquid, the liquid was stirred for 5 hours at room temperature, thus causing a reaction. After this reaction, a small amount of an aqueous solution of sodium hydrogencarbonate was added to the reacted mixture liquid, thus neutralizing the liquid. Then, 100 ml of dichloromethane was added to the neutralized liquid, thus obtaining an extract. This extract was washed with water and dried with sodium sulfate. The solvent was then distilled off under reduced pressure, thereby obtaining 40 g of white oily substance of 1,6- anhydro-β-D-galactopyranose-3,4-ethoxyacetal (5; R=ethyl) at a yield of 94%. This white oily substance exhibited the following physical properties:

1,6-anhydro-β-D-galactopyranose-3,4-ethoxyacetal (5)

1H NMR (ppm from TMS). $CH_3CH_2O$—; 1.23(3H,t), $CH_3CH_2O$—; 3.59 (2H,m), $CH(O—)_3$; 5.75 (1H,s), 1-position; 5.37 (1H,s), 2-position; 3.92 (1H,s), 3-position; 4.25 (1H,d), 4-position; 4.63 (1H,t), 5-position; 4.50 (1H,t), 6-position; 3.60 (1H,dd), 3.83 (1H,d).

$^{13}C$ NMR (ppm from TMS): 1-position; 100.8, 2-, 3-, 4-, and 5-position; 68.8, 69.5, 71.2, 74.4, 6-position; 63.4, $CH_3CH_2O$—; 14.7, $CH_3\underline{C}H_2O$—; 60,8, $\underline{C}H(O—)_3$; 114.4

[B] 40 g of 1,6-anhydro-β-D-galactopyranose-3,4-ethoxyacetal (5: R=ethyl) obtained in the step [A] was dissolved in 150 ml of acetic anhydride, thus preparing a solution. Then, 1 g of hydrous zirconium oxide was added to the solution, and the solution was heated and refluxed for 5 hours, thus causing a reaction therein. Upon completion of the the reaction, an aqueous solution of sodium hydrogencarbonate was added to the solution, thus neutralizing the solution. Then, 100 ml of dichloromethane was added to the neutralized solution, thereby obtaining an extract. This extract was washed with water and dried with sodium sulfate. Next, the solvent was distilled off under reduced pressure. Then the residue was distilled at 64° C. under a pressure of 2 mmHg, thereby obtaining 25 g of 1,6-anhydro-2-acetyl-3,4-dideoxy-β-D-galactopyranose (6) at a yield of 80%, in the form of a colorless oily substance. This substance had the following physical properties:

1,6-anhydro-2-acetyl-3,4-dideoxy-β-D-galactopyranose (6)

1H NMR (ppm from TMS): $CH_3CO$; 2.03 (3H,s), 1-position; 5.46 (1H,bs, J=1.93Hz), 2-position; 4.67 (1H,d,J=3.87Hz), 3-position; 5.70 (1H,ddd, J=1.93, 3.87, 9.86Hz), 4-position; 6.26 (1H,ddd,J=1.13, 4.71, 9.86Hz), 5-position; 4.69 (1H,dd,J=4.70, 4.0Hz), 6-position; 3.67 (1H,d, J=6.74Hz), 3.63 (1H,ddd,J=1.15, 6.74, 4.0Hz)

$^{13}C$ NMR (ppm from TMS): 1-position; 100.4, 2-position or 5-position; 69.3, 70.6, 3-position; 132.6, 4-position; 122.9, 6-position; 66.6, $\underline{C}H_3CO$; 21.2, $CH_3\underline{C}O$; 170.0

$[\alpha]_\alpha^{25}$ = −232.4 (c=0.95, chloroform)

[C] 25 g of 1,6-anhydro-2-acetyl-3,4-dideoxy-β-D-galactopyranose (6), obtained in the step [B] was dissolved in 100 ml of methanol, forming a solution. A small amount of sodium methoxide was added to the solution. The solution was stirred for one hour at room temperature, causing a reaction therein. Upon the completion the reaction, cation exchange resin was added to the solution, and the solution was stirred for 10 minutes. The insoluble substance was filtered off, and the solvent was distilled off under reduced pressure, whereby 19 g of 1,6-anhydro-3,4-dideoxy-β-D-galactopyranose (7) was obtained at a yield of 100%. This substance exhibited the following physical properties:

1,6-anhydro-3,4-dideoxy-β-D-galactopyranose (7)

¹H NMR (ppm from TMS): 1-position; 5.49 (1H,d,J=1.2Hz), 2-position; 3.67 (1H,m), 3-position; 5.78 (1H,ddd,J=1.2, 3.8, 9.8Hz), 4-position; 6.17 (1H,ddd,J=0.7, 4.8, 9.8Hz), 5-position; 4.69 (1H,ddd,J=1.2, 4.0, 4.70Hz), 6-position; 3.67 (m)

$^{13}C$ NMR (ppm from TMS): 1-position; 100.4, 2- or 5-position; 69.3, 70.6, 3-position; 132.6, 4-position; 122.9, 6-position; 66.6, $\underline{C}H_3CO$; 21.2, $CH_3 \underline{C}O$, 170.0

$[\alpha]_\alpha^{25}$ = −225.7 (c=0.779, dichloromethane)

[D] 19 g of 1,6-anhydro-3,4-dideoxy-β-D-galactopyranose (7) prepared in the step [C] was dissolved in 100 ml of dichloromethane, forming a solution. Then, 50 g of active manganese dioxide was added to this solution, and the solution was stirred for 2 at room temperature, thus causing a reaction. Upon completion of the reaction, manganese dioxide was filtered off, and the solvent was distilled off under reduced pressure, whereby 15.3 g of levoglucosenone (8) (i.e., 1,6-anhydro-3,4-dideoxy-β-D-glycero-hex-3-enopyranos-2-ulose) was obtained at a yield of 82%. This substance exhibited the following physical properties:

Levoglucosenone (8)
(1,6-anhydro-3,4-dideoxy-β-D-glycero-hex-3-enopyranos-2-ulose)

1H NMR (ppm from TMS): 1-position; 5.37 (1H,d,J=1.68Hz), 3-position; 6.13 (1H,dd,J=1.68, 9.88Hz), 4-position; 7.29 (1H,dd,J=4.67, 9.88Hz), 5-position; 5.03 (1H,t,J=4.67Hz), 6-position; 3.78 (1H,d,J=6.84), 3.91 (1H,dd,J=4.67, 6.84)

$^{13}C$ NMR (ppm from TMS): 1-position; 101.7, 2-position; 188.6, 3-position; 147.8, 4-position; 126.9, 5-position;71.8, 6-position; 66.6

$[\alpha]_\alpha^{25}$ = −534.2 (c=0.37, chloroform)

EXAMPLE 2

Steps, including reactions and refinings, were performed which were the same as those of Example 1, except that 1,6-anhydro-2-acetyl-β-D-galactopyranose-3,4-ethoxyacetal was used in place of 1,6-anhydro-β-D-galactopyranose-3,4-ethoxyacetal. As a result of this, 15.4 g of levoglucosenone was obtained from 50 g of D-galactopyranose anhydride, at a yield of 44.0%. The material, i.e., 1,6-anhydro-2-acetyl-β-D-galactopyranose-3,4-ethoxyacetal (5a), which is identified with the following formula, had been prepared by the method described below.

33 g of 1,6-anhydro-β-D-galactopyranose-3,4-ethoxyacetal (5: R=ethyl) was dissolved in 100 ml of acetic anhydride, along with a small amount of N,N-dimethylaminopyridine, thereby preparing a solution. This solution was stirred for 4 hours at room temperature, thus causing a reaction therein. Upon completion of the reaction, an aqueous solution of sodium hydrogencarbonate was added to the solution, thus neutralizing the solution. Then, 100 ml of dichloromethane was added to the neutralized solution, thereby obtaining an extract. This extract was washed with water and dried with sodium sulfate. Next, the solvent was distilled off under reduced pressure. Further, the residue was crystallized from ether, then the crystal was recrystallized from ether, thus obtaining 39 g of needle-shaped white crystal of 1,6-anhydro-2-acetyl-β-D-galactopyranose-3,4-ethoxyacetal (9), at a yield of 100%. This substance had the following physical properties:

1,6-anhydro-2-acetyl-β-D-galactopyranose-3,4-ethoxyacetal (9)

1H NMR (ppm from TMS): $CH_3CH_2O$—; 1.28 (3H,t,J=7.1Hz), $CH_3CO$; 2.12 (3H,s) $CH_3CH_2O$—; 3.74 (2H,m), $C\underline{H}(O—)_3$; 5.75 (1H,s), 1-position; 5.39 (1H,s), 2-position; 4.98 (1H,s), 3-position; 4.08 (1H,d.J=6.7Hz), 4-position; 4.42 (1H,t,J=6.1Hz); 5- position; 4.56 (1H,t,J=5.5Hz), 6-position; 3.64 (1H,dd,J=5.9, 7.6Hz), 4.60 (1H,d,J=6.1Hz)

$^{13}$C NMR (ppm from TMS): 1-position; 98.9, 2-, 3-, 4-, or 5-position; 69.9, 70.5, 72.1, 72.6, 6-position; 63.8, CH$_3$CH$_2$O—; 15,2, CH$_3$$\underline{C}$H$_2$O—; 61.3, $\underline{C}$H (O—)$_3$; 114.9, $\underline{C}$H$_3$CO; 21.0, CH$_3$$\underline{C}$O; 169.5 m.p.; 94.0° to 94.5° C.

$[\alpha]_a^{25} = -232.4$ (c=0.95, chloroform)

EXAMPLE 3

Steps, including reactions and refinings, were performed which were the same as those of Example 1, except that methyl ortho formate was used as an ortho formate in step [A]. As a result of this, 13.4 g of levoglucosenone (8) was obtained from 50 g of D-galactopyranose anhydride (1), at a yield of 38.3%.

The synthesized intermediate, i.e., 1,6-anhydro-2-acetyl-β-D-galactopyranose-3,4-methoxyacetal (5: R=methyl) exhibited the follow physical properties:

5-[1,6-anhydro-2-acetyl-β-D-galactopyranose-3,4-methoxyacetal

1H NMR (ppm from TMS): CH$_3$CH$_2$O—; 3.34 (3H,s), CH$_3$CO—; 2.13 (3H,s), C$\underline{H}$(O—)$_3$; 5.79 (1H,s), 1-position; 5.40 (1H,s), 2-position; 4.98 (1H,s), 3-position; 4.21 (1H,d,J=6.7Hz), 4-position; 4.62 (1H,dd,J=5.7, 6.7Hz); 5-position; 4.56 (1H,dd,J=4.2, 5.7Hz), 6-position; 3.65 (1H,dd,J=4.2, 7.9Hz), 3.90 (1H,d,J=7.9Hz)

$^{13}$C NMR (ppm from TMS): 1-position; 98.9, 2-, 3-, 4-, or 5-position; 69.9, 70.4, 72.1, 72.7, 6-position; 63.8, CH$_3$O—; 52.8, CH(O—)$_3$; 115.7, $\underline{C}$H$_3$CO—; 21.1, CH$_3$$\underline{C}$O—; 169.4

EXAMPLE 4

Steps, including reactions and refinings, were performed which were the same as those of Example 1, except that tetrahydrofuran was used in step [A] as an aprotic polar solvent in place of N,N-dimethylformamide. As a result, 11.4 g of levoglucosenone (8) was obtained from 50 g of D-galactopyranose anhydride (1), at a yield of 32.6%.

EXAMPLE 5

Steps, including reactions and refinings, were performed which were the same as those of Example 1, except that silica gel was used in step [B] as a catalyst in place of hydrous zirconium oxide. As a result, 12.6 g of levoglucosenone (8) was obtained from 50 g of D-galactopyranose anhydride (1), at a yield of 36.1%.

EXAMPLE 6

Steps, including reactions and refinings, were performed which were the same as those of Example 1, except that alumina was used in step [B] as a catalyst in place of hydrous zirconium oxide. As a result, 13.8 g of levoglucosenone (8) was obtained from 50 g of D-galactopyranose anhydride (1), at a yield of 39.4%.

EXAMPLE 7

Steps, including reactions and refinings, were performed which were the same as those of Example 1, except that an acetic acid was used in step [B] as catalyst in place of hydrous zirconium oxide. As a result, 13.2 g of levoglucosenone (8) was obtained from 50 g of D-galactopyranose anhydride (1), at a yield of 37.8%.

EXAMPLE 8

Steps, including reactions and refinings, were performed which were the same as those of Example 1, except that formic acid was used in step [B] as a catalyst in place of hydrous zirconium oxide. As a result, 10.5 g of levoglucosenone (8) was obtained from 50 g of D-galactopyranose anhydride (1), at a yield of 30.1%.

EXAMPLE 9

Steps, including reactions and refinings, were performed which were the same as those of Example 1, except that N,N-dimethylformamide was used in step [B] as an aprotic polar solvent in place of acetic anhydride. As a result, 14.3 g of levoglucosenone (8) was obtained from 50 g of D-galactopyranose anhydride (1), at a yield of 41.0%.

Additional advantages and modifications will readily occur to those skilled in the art. Therefore, the invention in its broader aspects is not limited to the specific details, and illustrated examples shown and described herein Accordingly, various modifications may be made without departing from the spirit or scope of the general inventive concept as defined by the appended claims and their equivalents.

What is claimed is:

1. A method of preparing levoglucosenone (8), comprising the steps of:

reacting 1,6-anhydro-β-D-galactopyranose (4), used as starting material, with ortho formate, thereby obtaining an ortho ester (5) of said starting material;

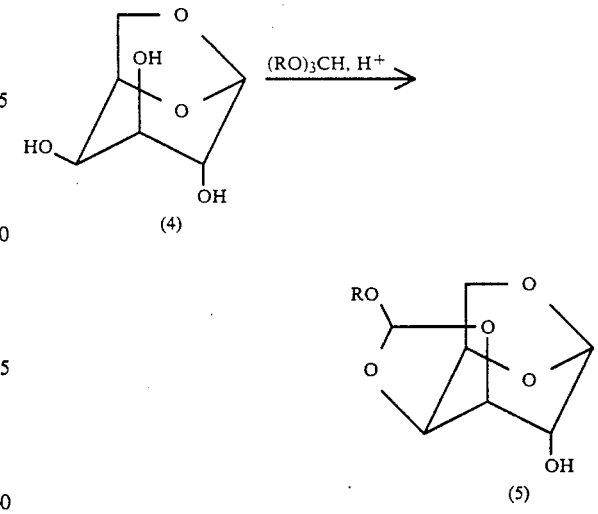

, wherein R represents CH$_3$ or C$_2$H$_5$, placing said ortho ester (5) under the conditions for a reductive elimination reaction of the ortho formate part of said ortho ester (5), thereby converting said ortho ester (5) to a 1,6-anhydro-3,4-dideoxy-β-D-galactopyranose (7); and

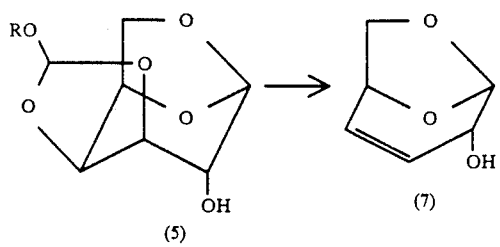

, wherein R has same meaning mentioned above, placing 1,6-anhydro-3,4-dideoxy-β-D-galactopyranose (7) under the conditions for oxidation of the hydroxy group of 1,6-anhydro-3,4-dideoxy-β-D-galactopyranose (7) thereby forming levoglucosenone (8);

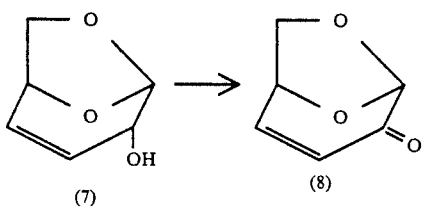

2. The method according to claim 1, wherein 1,6-anhydro-3,4-dideoxy-β-D-galactopyranose (4) is reacted with ortho formate in an aprotic polar solvent.

3. The method according to claim 2, wherein said aprotic polar solvent is one selected from the group consisting of N,N-dimethylformamide, tetrahydrofuran, 1,4-dioxane, and diglyme.

4. The method according to claim 1, wherein the reductive elimination reaction of the ortho formate part is performed by heating said ortho ester (5) in the presence of a catalyst.

5. The method according to claim 4, wherein said catalyst is an inorganic solid catalyst.

6. The method according to claim 5, wherein said inorganic solid catalyst is one selected from the group consisting of hydrous zirconium oxide, silica gel, and alumina.

7. The method according to claim 4, wherein said catalyst is an organic acid.

8. The method according to claim 7, wherein said organic acid is one selected from the group consisting of acetic acid and formic acid.

9. The method according to claim 1, wherein the oxidation of the hydroxy group of 1,6-anhydro-3,4-dideoxy-β-D-galactopyranose (7) is performed by using an oxidizing reagent.

10. The method according to claim 9, wherein said oxidizing reagent is active manganese dioxide.

11. The method according to claim 1, wherein said ortho ester (5) is converted to the acetate thereof by O-acetylation before conducting said reductive elimination reaction.

12. A method of preparing levoglucosenone (8), comprising the steps of:

reacting 1,6-anhydro-β-D-galactopyranose (4), used as starting material, with ortho formate, thereby obtaining an ortho ester (5) of said starting material;

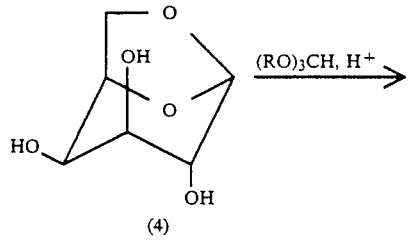

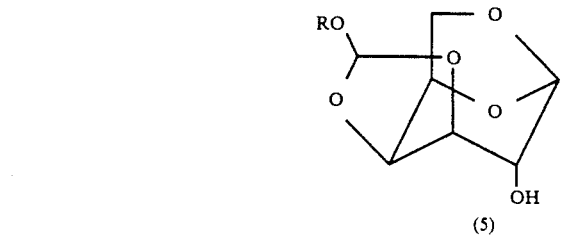

, wherein R represents $CH_3$ or $C_2H_5$, placing said ortho ester (5) under the conditions for a reductive elimination reaction of the ortho formate part of said ortho ester (5) in the presence of acetic anhydride or N,N-dimethylformamide, thereby converting said ortho ester (5) to a the dideoxy derivative (6);

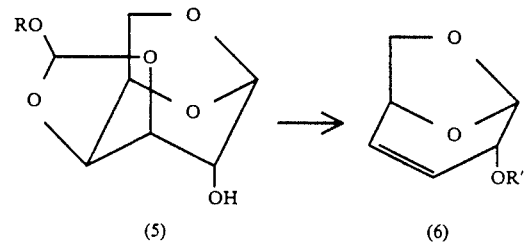

wherein R has same meaning mentioned above, and R' represents $CH_3CO$ or CHO, placing said dideoxy derivative (6) under the conditions for hydrolysis, thereby forming 1,6-anhydro-3,4-dideoxy-β-D-galactopyranose (7); and

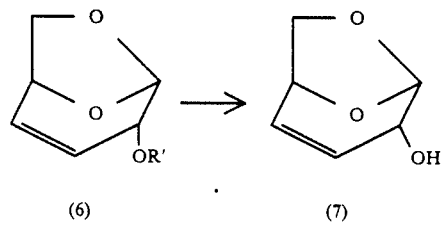

, wherein R' has same meaning mentioned above, placing 1,6-anhydro-3,4-dideoxy-β-D-galactopyranose (7) under the conditions for oxidation of the hydroxy group of said 1,6-anhydro-3,4-dideoxy-β-D-galactopyranose (7), thereby forming levoglucosenone (8).

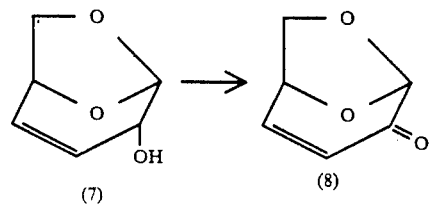

13. The method according to claim 12, wherein said ortho ester is converted to the acetate thereof by O-acetylation before conducting said reductive elimination reaction.

* * * * *